(12) United States Patent
McCardel

(10) Patent No.: US 8,657,829 B2
(45) Date of Patent: Feb. 25, 2014

(54) DEPTH GAUGE CUP IMPACTOR

(76) Inventor: Brian McCardel, Okemos, MI (US)

( * ) Notice: Subject to any disclaimer, the term of this patent is extended or adjusted under 35 U.S.C. 154(b) by 818 days.

(21) Appl. No.: 12/518,819

(22) PCT Filed: Dec. 21, 2007

(86) PCT No.: PCT/US2007/088553
§ 371 (c)(1),
(2), (4) Date: Jun. 11, 2009

(87) PCT Pub. No.: WO2008/080061
PCT Pub. Date: Jul. 3, 2008

(65) Prior Publication Data
US 2010/0016860 A1    Jan. 21, 2010

Related U.S. Application Data

(60) Provisional application No. 60/871,688, filed on Dec. 22, 2006.

(51) Int. Cl.
*A61B 17/58* (2006.01)
*A61B 17/60* (2006.01)
*A61F 2/00* (2006.01)

(52) U.S. Cl.
USPC ............................................. 606/91

(58) Field of Classification Search
USPC ............................................. 606/80, 91, 102
See application file for complete search history.

(56) References Cited

U.S. PATENT DOCUMENTS

| | | | |
|---|---|---|---|
| 6,132,469 A | 10/2000 | Schroeder | |
| 6,729,037 B2 | 5/2004 | White | |
| 2004/0215200 A1 | 10/2004 | Tornier et al. | |
| 2006/0015121 A1* | 1/2006 | Nielsen | 606/102 |
| 2008/0104855 A1* | 5/2008 | Kim et al. | 33/836 |

* cited by examiner

*Primary Examiner* — Sameh Boles
(74) *Attorney, Agent, or Firm* — Gifford, Krass, Sprinkle, Anderson & Citkowski, P.C.

(57) ABSTRACT

Disclosed apparatus and methods confirm the depth of insertion of an acetabular component in the course of a total Mp replacement using a graduated shaft through a cannulated holder. Embodiments are disclosed including a version integrated into existing instrumentation, and an alternative, disposable version, one per case. All of embodiments confirm appropriate seating of the acetabular component against the inner wall of the acetabulum. Given the hemispherical reaming that is done during acetabular preparation, this would allow for maximal contact between the prosthesis and the host bone.

15 Claims, 3 Drawing Sheets

DEPTH GAUGE CUP IMPACTOR

REFERENCE TO RELATED APPLICATION

This application claims priority from U.S. Provisional Patent Application Ser. No. 60/871,688, filed Dec. 22, 2006, the entire content of which is incorporated herein by reference.

FIELD OF THE INVENTION

This invention related generally to total hip replacement and, in particular, to apparatus and methods for confirming the depth of insertion of an acetabular component in the course of a total hip replacement.

BACKGROUND OF THE INVENTION

During total hip surgery, virtually all surgeons would like to confirm placement of the impacted acetabular component against tie inner wall of the acetabulum. For those surgeons that are using infrared-based "navigation" systems on a routine basis, this positional confirmation is effectively accomplished. In instances of minimally invasive surgery done with fluoroscopic assistance, this "seating" of the components may be confirmed radiographically.

For the majority of surgeons that do not use either method, however, a variety of ad hoc methods are currently employed. These techniques includes freehanded, thin wire depth gauge used for measurement of acetabular screw depth, a right-angle hemostat, or attempts at visual inspection. None of these approaches are particularly effective. Absent a navigation system or fluoroscopic confirmation, there is no reliable way to make this judgment.

SUMMARY OF THE INVENTION

This invention is directed to apparatus and methods for confirming the depth of insertion of an acetabalar component in the course of a total hip replacement. The apparatus is used in conjunction with an acetabular cup configured for total hip replacement, the cup having a central bore therethrough. A cannulated shaft is provided having a distal end adapted for coupling to the central bore of the cup and a proximal end including a reference point, line or surface. A rod insertable into the cannulated shaft has a distal tip that extends through the central bore of the cup and a proximal section with one or more markings that may be compared to the reference point, line or surface to determine how well the cup is seated in an acetabulum.

The cannulated shaft may be a separate component, or may form part of an impactor used to seat the cup in an acetabulum, in winch case the reference point may include a surface or marking on the proximal cap of the impactor. The cannulated shaft may be coupled to the central bore of the cup through a threaded connection or interference fit.

The rod may be provided as a sterilizable and reusable item, or as a pre-sterilized, disposable plastic item. Alternatively, the rod and shaft may together be provided as a pre-sterilized, disposable plastic unit. The rod includes multiple markings or a single marking corresponding to a cup of a predetermined size. The cup may have an outer bone-in-growth or -ongrowth surface.

A first method according to the invention of determining whether an acetabular cup is properly seated within an acetabulum comprises the steps of:
a) providing apparatus according to the invention wherein the cannulated shaft is separate from the impactor;
b) attaching the impactor instrument to the bore of the cup;
c) impacting the cup into an acetabulum using the impactor;
d) removing the impactor and installing the cannulated shaft to the bore of the cup;
e) inserting the graduated rod into the cannulated shaft until the distal tip of the rod makes contact with the surface of an acetabulum;
f) comparing the mark(s) on the rod to determine whether the cup is properly seated; and, if not:
g) removing the rod and shaft and repeating steps b)-f) as necessary until the cup is properly seated.

A second method according to the invention of determining whether an acetabular cup is properly seated within an acetabulum comprises the steps of:
a) providing apparatus according to the invention wherein the cannulated shaft forms part of an impactor;
b) impacting the cup into an acetabulum using the impactor without the rod inserted;
c) inserting the graduated rod into the cannulated shaft until the distal tip of the rod makes contact with the surface of an acetabulum;
d) comparing the mark(s) on the rod to determine whether tie cup is properly seated; and, if not:
e) repeating steps b)-d) as necessary until the cup is properly seated.

In some instances of the invention it may be known a priori which marking or markings are indicative of a properly seated cup. This would be the case, for example, when the cup, cannulated shaft and rod are supplied together. This may also be true if the shaft and rod are supplied as a unit, particularly if they are provided for use with a particular cup size. However, if the exact marking is not known, or if the practitioner wishes to confirm a measurement in advance, the invention may include the preliminary steps of attaching the cannulated shaft or cannulated impactor to the bore of the cup for test purposes; placing the cup on a firm surface with the rod inserted; and identifying a marking, or placing a marking on the shaft indicative of the cup bottoming out. This marling may then be used for comparison purposes during impaction with confidence that the cup will be properly seated.

All of embodiments allow for the confirmation of appropriate seating of the acetabular component against the inner wall of the acetabulum. Given the hemispherical reaming that is done during acetabular preparation, this would allow for maximal contact between the prosthesis and the host bone. The invention is particularly useful in conjunction with a "holeless" component since there is little opportunity to assess whether the component has "bottomed out."

DETAILED DESCRIPTION OF THE INVENTION

In broad and general terms, the devices described herein are used to measure the gap, if any, between an acetabular shell and the exposed acetabular surface.

According to a first embodiment of the invention, hereafter referred to as "integrated version," a movable and graduated shaft assembly is threaded into the central core of the acetabular implant as is currently done for cup insertion. This may be accomplished by providing a specialized cup having a threaded bore configured to receive the graduated shaft assembly or, alternatively, an existing implant may be used directly or drilled out and modified to accommodate the graduated shaft assembly. It is assumed that the outer, convex, bone-contacting surface of the implant includes a bone ingrowth or ongrowth surface appropriate to cementless fixation.

Figure 1:
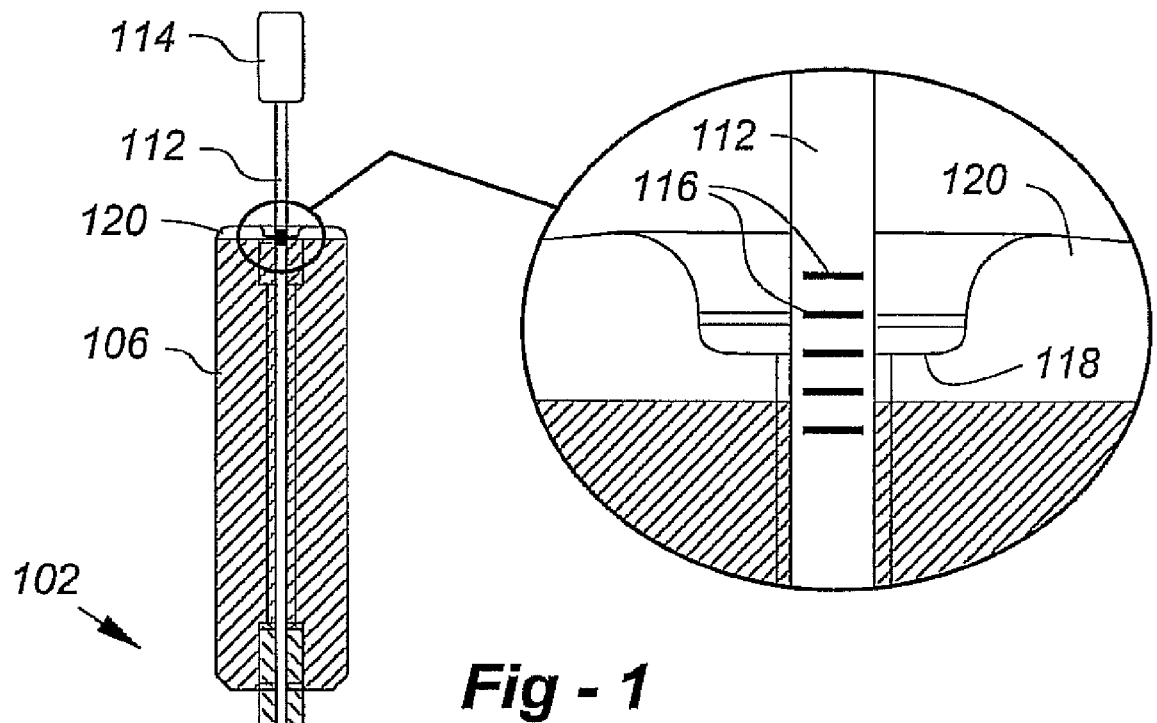
FIG. 1 is a simplified cross-sectional drawing of an integrated instrument according to the invention with detail insert diagrams.
Figure 1:
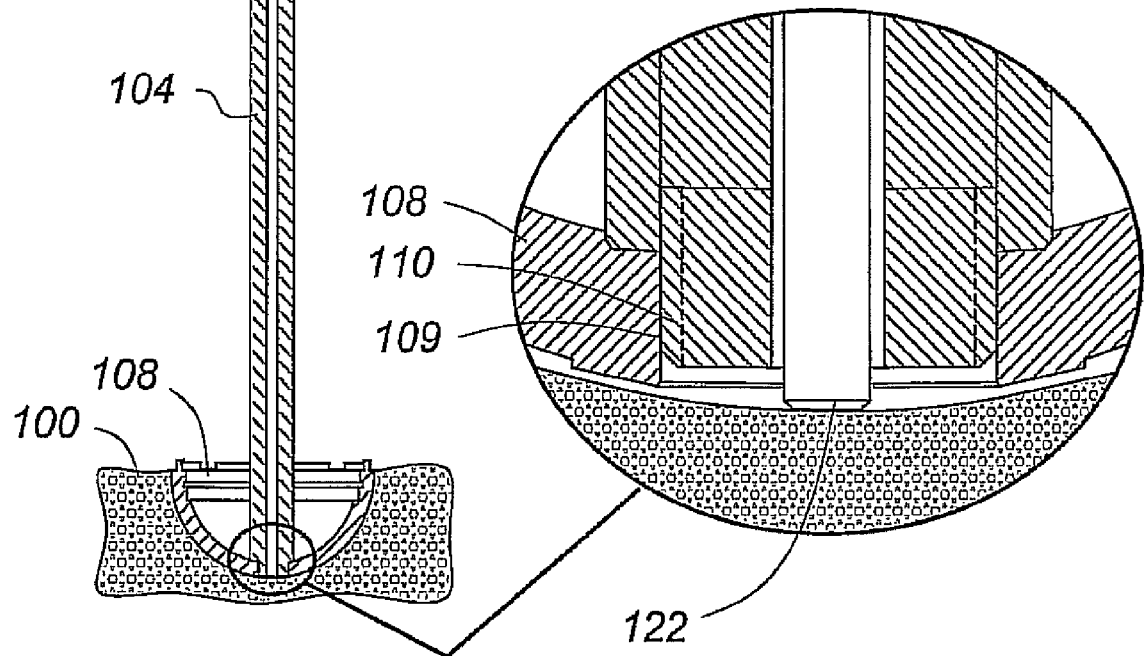

FIG. 1 is a drawing that shows the integrated version in partial cross section generally at 102. A simplified rendering of a reamed acetabulum is depicted at 100. The system includes a shaft 104 having a proximal end attached to impactor handle 106 and a distal end coupled to the acetabular cup 108, best seen in the enlarged inset drawing of the attachment itself at 110. While a threaded connection between tie shaft 104 and cup 108 is preferred, other couplings such as an interference fit may alternatively be used.

The shaft 104 and handle 106 are both cannulated, creating a lengthwise bore to receive gage rod 112 having optional rod handle 114. As best seen in the upper detail drawing, the rod includes one or more depth-related indicia 116. These indicia are compared to a reference point, line or surface 118 on the impactor cap 120, enabling the surgeon to know precisely how well the cup 108 is seated in the reamed acetabulum 100. In terms of materials, the impactor components must be substantial enough to withstand pounding; as such, sterilizable metals are preferred. The gage rod and option handle, however, may be metal or plastic.

The graduated rod 114 may be replaced with a rod having a single, size-specific mark; that is, each size cup would have a dedicated rod, thereby eliminating the need for initial measurements and would eliminate the need to "index" the depth for the specific cup prior to implantation. The gage rod in this embodiment would preferably be a sterilized plastic component for one-time use.

The cup 108 is implanted in the usual manner by pounding on impactor cap 120 without the gage rod 112 inserted. Once the implantable cup 108 is perceived to be seated in the bone, the rod 112 would be inserted into the drive handle, allowing the position relative to the underlying bone confirmed through contact to rod tip 122. This provides a reading against the exposed and graduated outer surface of the inner shaft, measuring the distance from the coated, backside of the cup to the wall of the reamed acetabulum. This allows for a confirmation that the implant is "flush" with the reamed acetabular surface. If not, the rod may be removed and the impactor cap stuck again, and re-measured as necessary until the cup is driven home.

Figure 2:
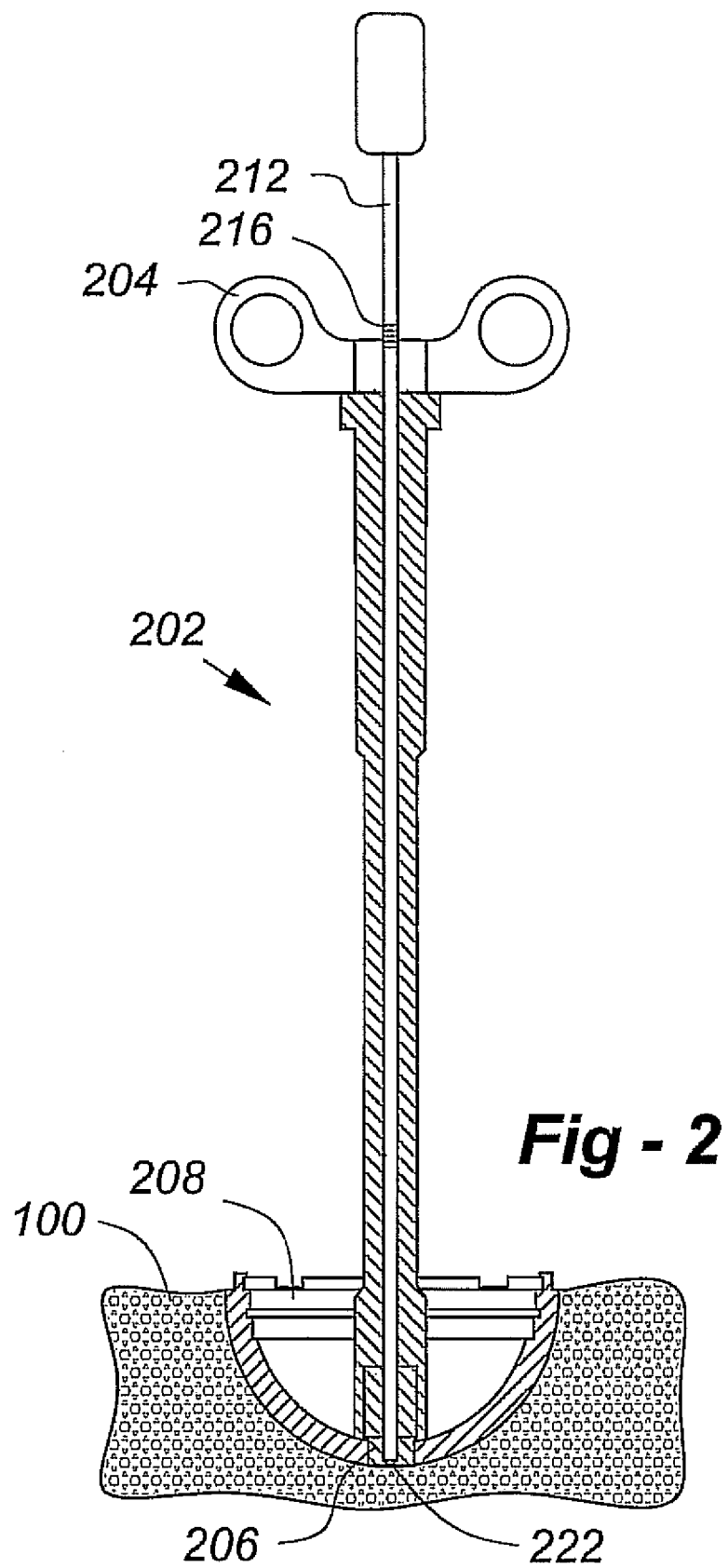
FIG. 2 shows a second embodiment of the invention in partial cross-section which is disposable.

FIG. 2 shows a second embodiment of the invention in partial cross section which is disposable. The device 202, which may include handles 204 reminiscent of a syringe, is threaded into the polar hole of the acetabular component at 206 after seating of the shell 208 and the removal of the impaction handle (not shown). This device would work in a similar manner to the integrated version, allowing for precise measurement of gap, if any, between the shell 208 and the wall of the acetabulum 200 by referring to mark(s) 216 on rod 212 when tip 222 bottoms out. Since this version is preferably disposable, all components may be plastic and provided in a sterile, sealed bag until use.

SURGICAL PROCEDURES

Integrated Version

1) Thread the impaction drive handle 104 into the polar hole of the implant 108 until fully seated, Confirmation of full seating is important to prevent threads shearing off of the impactor or the implant, as per current use recommendations.

2) Confirm the position of the 108 as being flush with the external surface of the acetabular component and identify the mark(s) 116 on the graduated shaft 112 that correspond to the depth gauge being "flush." (If the size-specific embodiment is used, the surgeon must first obtain a sterile, disposable depth gauge appropriate for the specific cup to be implanted.)

3) Remove the depth gauge.

4) Impact the acetabular component into the reamed acetabulum.

5) Once the component feels seated, test for stability per current practice.

6) Once satisfied with the stability, confirm that the component is seated against the inner wall of the acetabulum by inserting the depth gauge into the impaction handle, and determine the gap, if any, between the acetabulum and the component.

7) If necessary, make appropriate changes to the component position by further impacting the cup, and repeat steps 5 and 6 as necessary until satisfied with depth of impaction.

Disposable Version:

1) Place implant and test for stability as per usual.

2) After the removal of the impaction handle, thread disposable measuring device into polar hole of the acetabular component.

3) Depress plunger, and measure distance, if any, between the reamed acetabulum and the implanted component.

4) Make appropriate changes and repeat steps as necessary.

Figure 3:
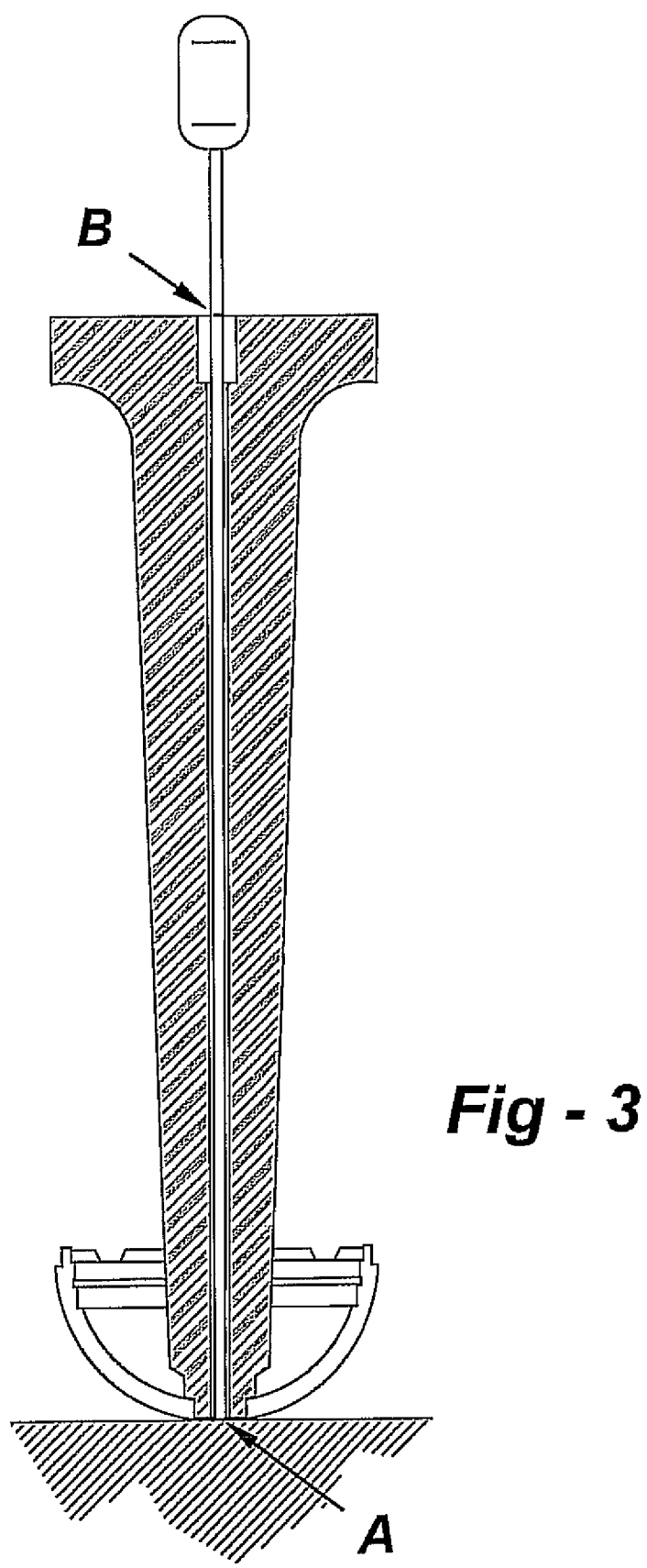
FIG. 3 shows how the correct marking may be determined by placing the cup and measurement assembly against a firm surface prior to use in situ.

In both of the procedures outlined above, and as discussed in the Summary of the Invention, if the exact marking is not known, or if the practitioner wishes to confirm a measurement in advance, the protocol may include the preliminary steps of attaching the cannulated shaft or cannulated impactor to the bore of the cup for test purposes; placing the cup on a fen surface with the rod inserted; and identifying a marking, or placing a marking on the shaft indicative of the cup bottoming out at "A" in FIG. 3. This marking "B" may then be used for comparison purposes during impaction with confidence that the cup will be properly seated. Although FIG. 3 depicts a different design according to the invention the technique is applicable to all of the disclosed embodiments.

I claim:

1. Orthopaedic apparatus adapted for use with an acetabular cup having a central bore therethrough, the acetabular cup being an implant intended for implantation into a living body, the apparatus comprising:
    a cannulated shaft having a distal end removably attached to the central bore of the implant and a proximal end including a reference point, line or surface; and
    a rod insertable into the cannulated shaft, the rod having a distal tip that extends through the central bore of the implant and a proximal section with one or more markings that may be compared to the reference point to determine how well the cup is seated in an acetabulum.

2. The apparatus of claim 1, wherein the cannulated shaft forms part of an impactor used to seat the implant in an acetabulum.

3. The apparatus of claim 1, wherein:
    the cannulated shaft forms part of an impactor having a proximal cap used to seat the implant in an acetabulum; and
    the reference point, line or surface is on the proximal cap.

4. The apparatus of claim 1, wherein:
the cannulated shaft is removably attached to the central bore of the implant through a threaded connection.

5. The apparatus of claim 1, wherein the rod is a pre-sterilized, disposable plastic item.

6. The apparatus of claim 1, wherein the rod includes a single marking corresponding to a implant of a predetermined size.

7. The apparatus of claim 1, wherein the implant has an outer bone-ingrowth or bone-ongrowth surface.

8. The apparatus of claim 1, further including:
an acetabular implant having a threaded central bore; and
wherein the distal end of the cannulated shaft is threaded to match the threaded bore.

9. Orthopaedic apparatus, comprising:
an acetabular cup configured for implantation as part of a total hip replacement, the cup having a central bore therethrough;
a cannulated shaft having a distal end adapted for coupling to the central bore of the cup and a proximal end including a reference point, line or surface; and
a rod insertable into the cannulated shaft, the rod having a distal tip that extends through the central bore of the cup and a proximal section with one or more markings that may be compared to the reference point to determine how well the cup is seated in an acetabulum.

10. The apparatus of claim 9, wherein the cannulated shaft forms part of an impactor used to seat the cup in an acetabulum.

11. The apparatus of claim 9, wherein:
the cannulated shaft forms part of an impactor having a proximal cap used to seat the cup in an acetabulum; and
the reference point, line or surface is on the proximal cap.

12. The apparatus of claim 9, wherein:
the cannulated shaft is coupled to the central bore of the cup through a threaded connection.

13. The apparatus of claim 9, wherein the rod is a pre-sterilized, disposable plastic item.

14. The apparatus of claim 9, wherein the rod includes a single marking corresponding to a cup of a predetermined size.

15. The apparatus of claim 9, wherein the cup has an outer bone-ingrowth or bone-ongrowth surface.

* * * * *